United States Patent [19]

Harada

[11] Patent Number: 5,089,005
[45] Date of Patent: Feb. 18, 1992

[54] CATHETER FOR THE INTRODUCTION OF AN EXPANDABLE MEMBER

[75] Inventor: Fumiaki Harada, Fuji, Japan
[73] Assignee: Terumo Kabushiki Kaisha, Tokyo, Japan
[21] Appl. No.: 465,179
[22] Filed: Feb. 8, 1990
[30] Foreign Application Priority Data
 Aug. 13, 1987 [JP] Japan .................. 62-202397
[51] Int. Cl.⁵ .................................... A61M 29/00
[52] U.S. Cl. ...................... 606/194; 606/192; 604/104
[58] Field of Search .............. 604/104–109, 604/8; 606/191–192, 194, 198; 623/1, 12

[56] References Cited

U.S. PATENT DOCUMENTS

| | | |
|---|---|---|
| 4,503,569 | 3/1985 | Dotter . |
| 4,762,128 | 8/1988 | Rosenbluth . |
| 4,830,003 | 5/1989 | Wolff et al. .......... 604/191 |
| 4,893,623 | 1/1990 | Rosenbluth . |
| 4,969,890 | 11/1990 | Sugita et al. ........ 623/1 X |

FOREIGN PATENT DOCUMENTS

| | | |
|---|---|---|
| 0033659A2 | 8/1981 | European Pat. Off. . |
| 61-6655 | 2/1986 | Japan . |
| 62-82975 | 4/1987 | Japan . |
| 63-214264 | 9/1988 | Japan . |

OTHER PUBLICATIONS

Encyclopedia of Chemical Technology, 3rd Ed, vol. 20, 1982/John Wiley and Sons; NY, NY), "Shape-Memory Alloys" (pp. 726–736).

Patent Abstracts of Japan, vol. 1, No. 17, 3rd Jan. 1986; & JP-A-60169 551 (Hitachi Kinzoku K.K.) 03-09-1985, Abstract.

R. B. Galland, "Surgical Management of Radiation Enteritis", 1986, pp. 199–205, vol. 99, Surgery.

*Primary Examiner*—John D. Yasko
*Assistant Examiner*—Corrine Maglione
*Attorney, Agent, or Firm*—Frishauf, Holtz, Goodman & Woodward

[57] ABSTRACT

A catheter includes a cylindrical expansion holder detachable from its distal end portion to temporarily or permanently expand and hold an inner diameter of an internal cavity of a blood vessel or any other tubular organ. The outer diameter of the distal end portion of the catheter which supports the expansion holder is much smaller than that of other catheter portions. Even if the cylindrical expansion holder is supported on the small-diameter portion, the outer diameter of the expansion holder is equal to or smaller than that of other catheter portions. The expansion holder is made of a shape memory alloy which can radially expand or contract in accordance with changes in temperature. The expansion holder can expand or contract by supplying a warm or cool solution from side holes formed in the distal end portion of the catheter and bringing this solution into contact with the expansion holder.

7 Claims, 2 Drawing Sheets

CATHETER FOR THE INTRODUCTION OF AN EXPANDABLE MEMBER

TECHNICAL FIELD

The present invention relates to a catheter for inserting or removing an expansion holder for holding an inner diameter of an internal cavity of a tubular organ.

BACKGROUND ART

An expansion holder (to be also called a stent hereinafter) is generally used to hold an internal diameter of an internal cavity of a tubular organ so as to prevent a stenosed portion of, e.g., a coronary artery from being stenosed again after the stenosed portion is expanded by a blood vessel expansion catheter.

A conventional stent used for the above purpose is a net made of a stainless steel wire (Surgery, 1986, Vol. 99, No. 2, p. 199-205) or a stent made of a unidirectional shape memory alloy (Published Examined Japanese Patent Application No. 61-6655). When a blood vessel is to be held expanded by using this stainless steel stent, the stent is inserted to a predetermined position of the blood vessel through a blood vessel expansion catheter, and a balloon arranged at the distal end of the catheter is expanded to expand the stent to the same diameter of the blood vessel. When a stent made of a unidirectional shape memory alloy is used, it is inserted to a predetermined position of a blood vessel and is warmed with warm water, thereby expanding the stent.

In either case, the stent is simply wound around and held at the distal end portion of the catheter. The outer diameter of a catheter portion around which the stent is wound is larger than that of other catheter portions. As a result, when a catheter is inserted in a relatively thin blood vessel such as a coronary artery, or when the catheter mounted with this stent is inserted into a guide catheter, the sliding operation of the catheter is degraded due to the presence of the stent mounting portion, thus posing a problem. In addition, since a conventional stent inserting/removing catheter does not have any means for assuring a position of the distal end of the catheter or a positional relationship between the catheter distal end and the indwelled stent, it is difficult to operate such a conventional catheter.

It is an object of the present invention to provide a stent inserting/removing catheter which can be smoothly slid within a blood vessel and in a guide catheter, can assure a position of a distal end portion, and can improve operability.

DISCLOSURE OF INVENTION

In order to solve the above problem, the present invention reduces the outer diameter of a stent mounting portion at a distal end portion of a catheter to prevent this mounting portion from having an outer diameter larger than that of other catheter portions even if a stent is mounted thereon, and employs a means for forming an X-ray non-transmission marker on a small-diameter portion of the stent mounting portion, as needed.

More specifically, according to the present invention, there is provided a catheter characterized by comprising a catheter tube having an open proximal end or two open ends and at least one side opening formed on a circumferential wall near a distal end of the catheter tube to communicate with an opening at the proximal end, a hub portion formed to communicate with the opening at the proximal end of the catheter tube, and an expansion holder for holding an inner diameter of an internal cavity of a tubular organ, the expansion holder being made of a shape memory alloy cylinder which can radially expand or contract upon changes in temperature, and the expansion holder being mounted to cover at least part of a catheter tube portion corresponding to the side opening, wherein an outer diameter of the catheter tube portion corresponding to the side opening is smaller than that of other catheter tube portions. The expansion holder can be mounted on the catheter tube portion corresponding to the side opening so that an outer diameter of the expansion holder is equal to or smaller than that of the other catheter tube portions.

Furthermore, according to the present invention, there is provided a catheter having an X-ray non-transmissing marker on at least part of the catheter tube portion corresponding to the side opening.

Moreover, according to the present invention, there is provided the expansion holder comprising a helical member made of a unidirectional or bidirectional shape memory alloy.

The hub portion of the catheter may comprise a branched hub having at least one branch port. A check valve may be arranged in one of the ports.

The shape memory alloy according to the present invention has a transformation temperature and is deformed into a memory shape when it is heated to the transformation temperature or more. The unidirectional shape memory alloy can be freely deformed at the transformation temperature or less, and keeps the memory shape upon being heated to the transformation temperature or more even when the alloy is cooled to the transformation temperature or less unless an external force is not applied thereto. The bidirectional shape memory alloy additionally has a memory shape at the transformation temperature or less and is reversively deformed into one of the two shapes with respect to the transformation temperature as a boundary.

In the catheter according to the present invention, since the stent can be mounted on a catheter tube portion near its distal end such that the outer diameter of the stent mounting portion is not larger than that of other catheter tube portions, sliding resistance can be greatly reduced when the catheter tube is inserted into the guide catheter or a blood vessel, thereby improving operability. In addition, since the marker made of an X-ray non-transmission material is formed on the stent mounting portion, the position of the distal end of the catheter or the relationship between the indwelled stent and the distal end of the catheter can be clearly assured. Other additional effects can also be obtained. For example, when branch ports are formed in the hub portion, a cooling liquid or various liquid medicine solutions can be injected without requiring removal of a circuit device for measuring a pressure and the like.

BEST MODE OF CARRYING OUT THE INVENTION

The present invention will be described with reference to the illustrated embodiment.

Figure 1:
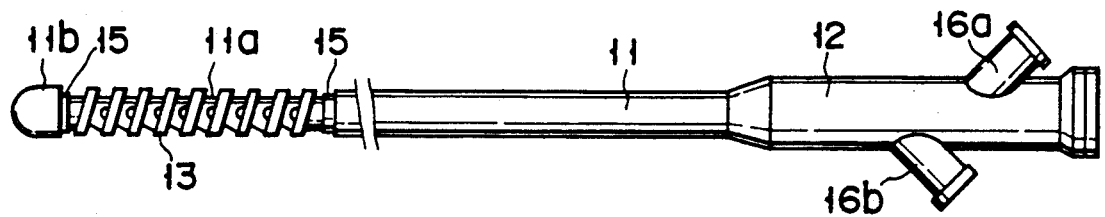
FIG. 1 is a side view of a catheter according to the present invention.

FIG. 1 shows an embodiment of a catheter according to the present invention. The catheter comprises a catheter tube 11 having two open ends, a hub portion 12 arranged to communicate with an opening at the proximal end of the catheter tube 11, and a spiral expansion holder (stent) 13 mounted on the distal end portion of the catheter tube 11. A portion of the catheter tube 11 which receives the stent 13 thereon constitutes a small-diameter portion 11a having an outer diameter smaller than that of other catheter tube portions. Therefore, when the stent 13 is mounted on the small-diameter portion 11a, the outer diameter of the stent 13 is equal to or smaller than that of other catheter tube portions. In other words, the outer diameter of the small-diameter portion 11a of the catheter tube 11 is smaller than the outer diameter of other catheter tube portions by an amount corresponding to twice or more the wall thickness of the stent 13.

Figure 2:
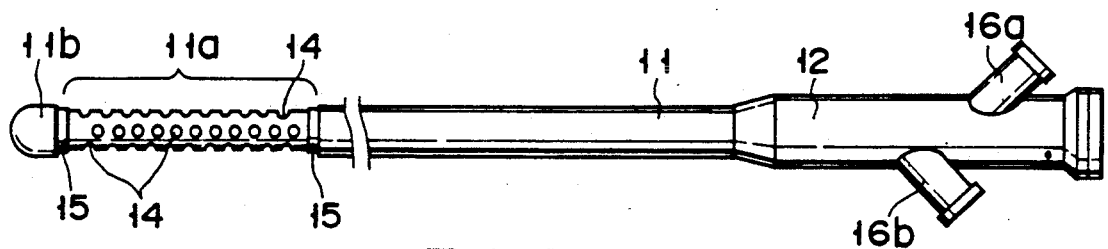
FIG. 2 is a side view showing a state wherein a stent is removed from the catheter.

A large number of side openings 14 which communicate with the opening at the proximal end of the catheter tube 11 to supply a stent cooling liquid are formed in the circumferential wall surface of the small-diameter portion 11a. FIG. 2 shows a state wherein the spiral stent 13 (FIG. 3) is removed from the assembly shown in FIG. 1, thus clearly illustrating the state of the side openings 14. The shape of each side opening 14 is not limited to the illustrated circular shape, but may be a slit-like shape. In addition, the number of side openings 14 is not limited to a specific number, but can be arbitrarily selected.

A distal end portion 11b of the catheter tube 11 has an outer diameter equal to that of the proximal portion and has a spherical end face. A hole is formed at the center of the distal end portion 11b to receive a guide wire therethrough. Ring markers 15 made of an X-ray non-transmission material such as gold are formed at both ends of the small-diameter portion 11a.

Figure 4:
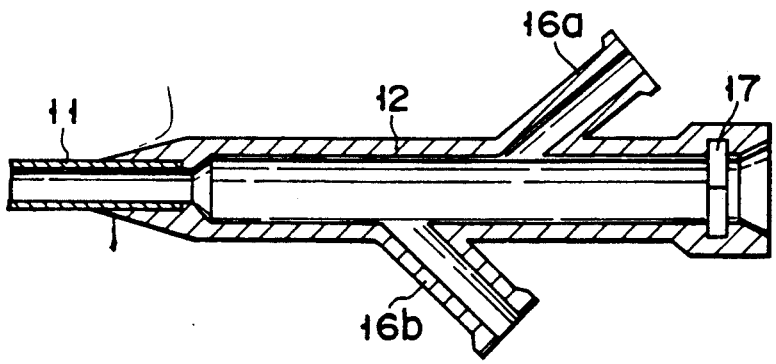
FIG. 4 is an enlarged sectional view of a hub portion of the catheter.

The hub portion 12 has a pair of branch ports 16a and 16b, so that a cooling liquid and liquid medicine can be injected without removing a pressure measuring circuit device and the like. Alternatively, only one branch port may be provided, and a three-port cock or the like may be mounted in this branch port. As shown in FIG. 4, the proximal end of the hub portion 12 is open and a check valve 17 made of a flexible material such as silicone rubber is arranged near the opening of the proximal end. Therefore, the guide wire or the like can be inserted through the proximal end of the hub portion 12 while maintaining liquid tightness.

Generally, a thermoplastic resin (e.g., an ethylene-vinyl acetate copolymer) is preferably used as a material of the catheter tube 11. Similarly, a thermoplastic resin (e.g., polycarbonate) is generally used to form the hub portion 12. As shown in FIG. 4, the hub portion 12 is connected to the proximal end portion of the catheter tube 11.

EXAMPLE 1

Figure 3:
FIG. 3 is a side view showing a structure of the stent.
Figure 5:
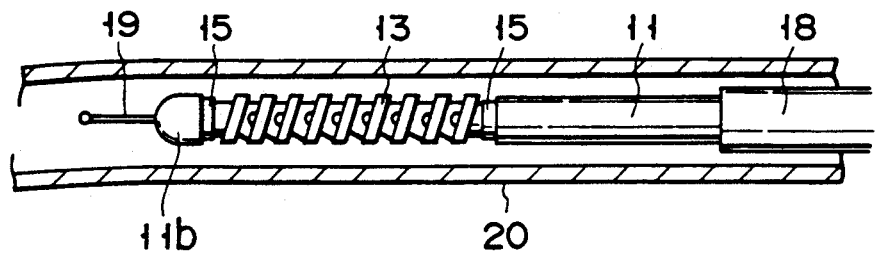
FIG. 5 is a side view showing a state wherein the catheter according to the present invention is inserted into a blood vessel, and FIG. 6 corresponds to FIG. 5 and is a side view showing a state wherein the stent is expanded and indwelled in the blood vessel.
Figure 6:
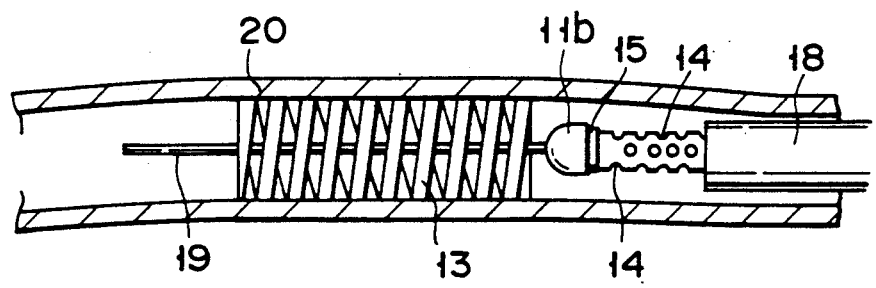

A bidirectional shape memory alloy (a Ni-Ti binary alloy consisting essentially of 51 atm % of Ni and the balance substantially Fe) manufactured into a stent 13 by a predetermined method was formed into a spiral shape, as shown in FIG. 3, and the spiral stent 13 was inserted around the small-diameter portion 11a of the catheter tube 11 in an expanded shape while being maintained at 35° C. or more. The expanded stent 13 was cooled to a temperature of 20° C. or less by using a physiological saline cooled with ice and contracted and was brought into tight contact with the small-diameter portion 11a. The outer diameter of the stent 13 was thus set to be equal to or slightly smaller than that of other portions of the catheter tube 11. The physiological saline cooled with ice was flowed out from the side openings 14 through the port 16b. As shown in FIG. 5, the stent 13 was inserted to the target indwelling portion through the guide catheter 18 by utilizing the guide wire 19 while the stent 13 was kept contracted. In this case, the guide catheter 18 was inserted in a blood vessel 20 in advance. This operation was performed under X-ray transmission fluoroscopy. The position of the stent 13 was easily confirmed by the markers 15 mounted on the small-diameter portion 11a of the catheter tube 11. When the stent 13 reached this indwelling portion, and supply of the physiological saline cooled with ice was stopped, the stent 13 was gradually warmed by the body temperature. When the small-diameter portion was warmed to the body temperature (35° C.), the stent 13 was expanded, and was brought into contact with the inner wall surfaces of the blood vessel 20, and was held at this position, as shown in FIG. 6. The distal end of the catheter tube 11 could be easily removed from the stent 13 while the stent 13 was indwelled at a predetermined position of the blood vessel 20. When a predetermined period of time elapsed after the indwelling operation, the catheter tube 11 was inserted into the blood vessel 20 again, and a contrast medium was injected into the blood vessel 20 through the port 16a to check whether thrombi or the like were attached to the stent 13. If so, an appropriate infusion solution such as urokinase was injected from the port 16a to dissolve the thrombi. The physiological saline cooled with ice was injected from the port 16b to cool and contract the stent 13. The stent 13 was brought into contact with the small-diameter portion 11a of the catheter tube 11 and could be removed from the indwelling portion.

EXAMPLE 2

A unidirectional shape memory alloy (a Ni-Ti binary alloy consisting essentially of 50 atm % of Ni and the balance substantially Fe) manufactured into a stent 13 by a predetermined method was formed into a spiral shape, as shown in FIG. 3. A shape was memorized such that this stent 13 could be deformed to be brought into contact with the small-diameter portion 11a of the catheter tube 11 at 40° C. or less but was expanded at 50° C. or more to be brought into contact with a predetermined indwelling portion.

As shown in FIG. 1, the stent 13 was brought into tight contact with the small-diameter portion 11a of the catheter tube 11 to set the outer diameter of the stent 13 to be equal to or smaller than that of other portions of the catheter tube 11, as shown in FIG. 1. As shown in FIG. 5, the stent 13 was inserted to the target indwelling portion through the guide catheter 18. A contrast medium was injected from the port 16b, and a stenosed portion at the indwelling portion was checked by transmission scopy at the same time pressures at the proximal and distal end portions of this portion were measured via the port 16a to appropriately determine the degree of stenosis. Liquid medicine such as urokinase was injected from the port 16b, and an appropriate treatment was performed for the indwelling portion. A warm physiological saline at 50° C. or more was supplied from the port 16b to the side openings 14 to change the shape of the stent 13 in an expanded shape and to indwell the stent 13 at this portion. Thereafter, a contrast medium was injected from the port 16b to check indwelling of the stent under fluoroscopy, and at the same time pressures at the proximal and distal end portions of the indwelling portion were measured via the port 16a to confirm there was no pressure gradient. The catheter 11 was then removed from the body.

INDUSTRIAL APPLICABILITY

The catheter according to the present invention is useful in medical operations which aim at temporarily or permanently expanding and holding the inner diameter of an internal cavity of a blood vessel or any other tubular organ.

I claim:

1. A catheter comprising:
    a catheter tube having:
        an open proximal end and an open distal end;
        first and second catheter tube portions, respectively having first and second outer diameters, said first and second catheter tube portions being positioned adjacent to each other with said first tube portion being positioned adjacent said distal end of said catheter tube, said first outer diameter of said first catheter tube portion being smaller than the second outer diameter of said second catheter tube portion; and
        at least one side opening in said first catheter tube portion, said at least one side opening being in communication with said open proximal end of said catheter tube;
    a hub portion communicating with said open proximal end of said catheter tube;
    a check valve coupled to said hub portion; and
    an expansion holder for holding open an inner diameter portion of an internal cavity of a tubular organ of a patient, said expansion holder comprising a shape memory alloy having a substantially cylindrical shape which radially expands and contracts with changes in temperature;
    said expansion holder covering at least a portion of said first catheter tube portion adjacent said at least one side opening; and
    said expansion holder when unexpended, having an outer diameter which does not exceed said second outer diameter of said second catheter tube portion.

2. A catheter according to claim 1, wherein at least one X-ray non-transmission marker is provided on said first catheter tube portion.

3. A catheter according to claim 1, wherein said hub includes at least one port.

4. A catheter according to claim 1, further comprising an end portion at said distal end of said catheter tube, said end portion having an outer diameter substantially equal to that of said second catheter tube portion.

5. A catheter according to claim 1, wherein said expansion holder has a helical shape.

6. A catheter according to claim 1, wherein said expansion holder comprises a unidirectional shape memory alloy.

7. A catheter according to claim 1, wherein said expansion holder comprises a bidirectional shape memory alloy.

* * * * *